(12) United States Patent
Alothman et al.

(10) Patent No.: US 9,217,732 B2
(45) Date of Patent: Dec. 22, 2015

(54) NANOFLOW DETECTOR CELL

(75) Inventors: Zeid Abdullah Alothman, Riyadh (SA); Ahmed-Yacine Badjah Hadj Ahmed, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 330 days.

(21) Appl. No.: 13/876,839

(22) PCT Filed: Oct. 4, 2010

(86) PCT No.: PCT/IB2010/054459
§ 371 (c)(1),
(2), (4) Date: Mar. 28, 2013

(87) PCT Pub. No.: WO2012/046096
PCT Pub. Date: Apr. 12, 2012

(65) Prior Publication Data
US 2013/0186187 A1    Jul. 25, 2013

(51) Int. Cl.
| | |
|---|---|
| *G01N 13/00* | (2006.01) |
| *G01N 30/84* | (2006.01) |
| *G01N 30/04* | (2006.01) |
| *G01N 21/05* | (2006.01) |
| *G01N 30/74* | (2006.01) |
| *B29C 70/68* | (2006.01) |
| *G01N 30/60* | (2006.01) |
| *G01N 21/03* | (2006.01) |
| *B82Y 40/00* | (2011.01) |

(52) U.S. Cl.
CPC .............. *G01N 30/04* (2013.01); *B29C 70/68* (2013.01); *G01N 21/05* (2013.01); *G01N 30/74* (2013.01); *B82Y 40/00* (2013.01); *G01N 30/6095* (2013.01); *G01N 2021/0346* (2013.01); *Y10S 977/70* (2013.01); *Y10S 977/888* (2013.01)

(58) Field of Classification Search
CPC .... G01N 21/05; G01N 30/74; G01N 30/6095
USPC .......................... 73/61.53, 61.55, 61.56, 61.58
See application file for complete search history.

(56) References Cited

U.S. PATENT DOCUMENTS

| | | |
|---|---|---|
| 3,795,450 A | 3/1974 | Munk |
| 4,847,207 A | 7/1989 | Birks et al. |
| 5,292,483 A | 3/1994 | Kaye |
| 5,423,513 A | 6/1995 | Chervet et al. |

(Continued)

OTHER PUBLICATIONS

Authors: Pawel L. Urban, David M. Goodall, Alexandre Z. Carvalho, Edmund T. Bergstrom, Ann Van Schepdael and Neil C. Bruce, Title: "Multi-compound electrophoretic assays for tyramine oxidase with a UV area detector imaging multiple windows on a looped capillary", Date: 2008, Publisher: Elsevier, Journal of Chromatography A, 1206, pp. 52-63.*

(Continued)

*Primary Examiner* — Lisa Caputo
*Assistant Examiner* — Roger Hernandez-Prewitt
(74) *Attorney, Agent, or Firm* — Richard C Litman

(57) ABSTRACT

A nanoflow detector cell comprises a nanoflow detection cell template defining a sample channel transverse template and a reference channel transverse template, generally parallel to the sample channel, and spaced apart from the sample channel. Clear capillary tubing extends through the sample channel, defining a sample chamber, a portion of the capillary tubing extends out of each end of the sample channel, and is shaped to the template.

18 Claims, 3 Drawing Sheets

(56) References Cited

U.S. PATENT DOCUMENTS

| | | | |
|---|---|---|---|
| 5,757,482 A * | 5/1998 | Fuchs et al. | 356/246 |
| 5,776,481 A | 7/1998 | Karst et al. | |
| 6,989,129 B2 | 1/2006 | Licklider et al. | |
| 7,050,660 B2 * | 5/2006 | Cyr et al. | 385/12 |
| 2005/0257885 A1 * | 11/2005 | Hobbs | 156/293 |
| 2009/0046282 A1 * | 2/2009 | Hong | 356/246 |

OTHER PUBLICATIONS

Authors: Bruno E. Lendi and Veronika R. Meyer, Title: "The UV Detector for HPLC—An ongoing Success Story", Date: 2005, Publication: LCoGC Europe, vol. 18(3), pp. 156-163.*

Authors: Gerard Rozing, Maria Serwe, Hans-Georg Weissgerber and Bernd Glatz, Title: "A system and columns for capillary HPLC", Date: May 2001, Publisher: Agilent Technologies, Publication No. 5988-3282EN, pp. 1-10.*

* cited by examiner

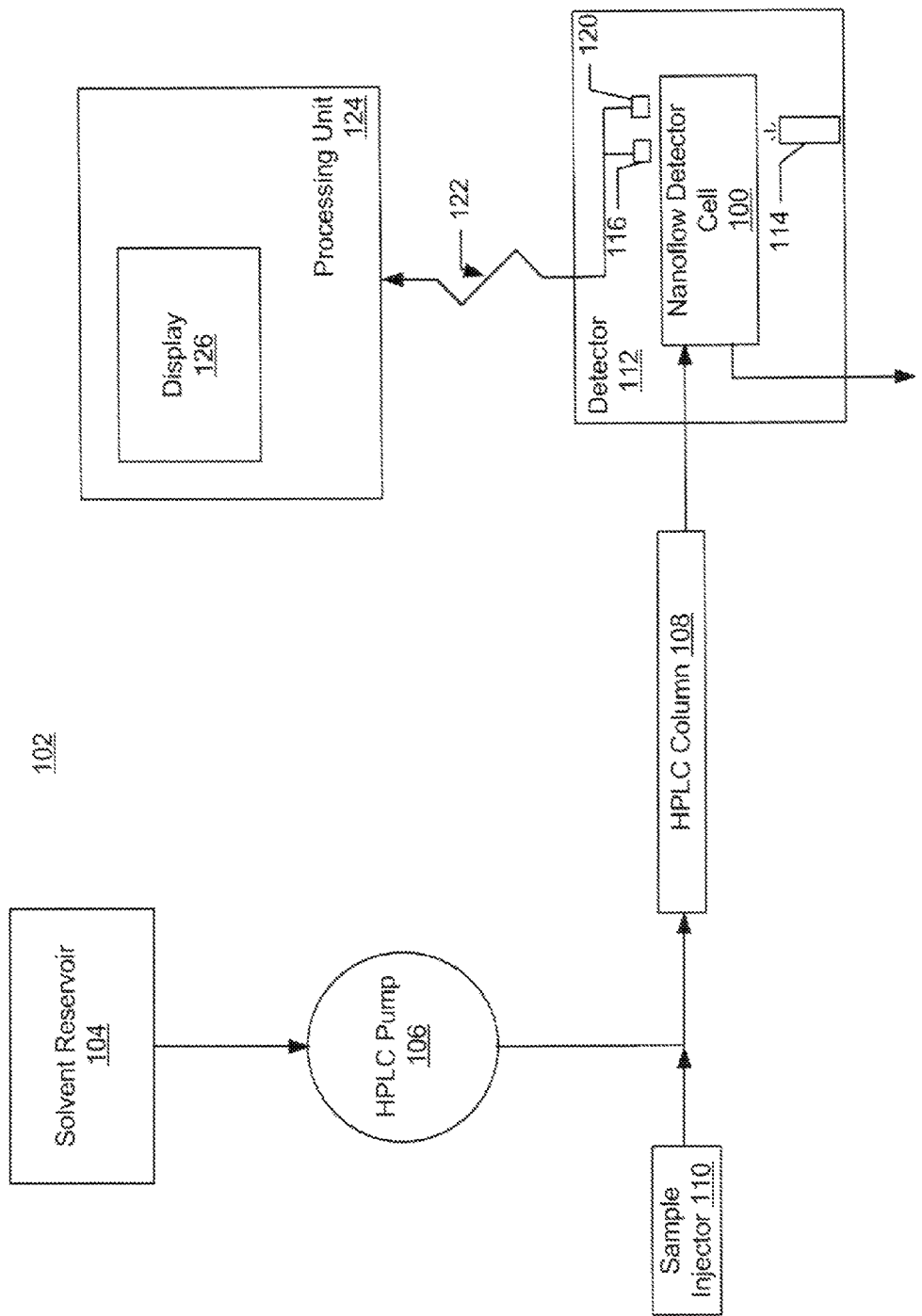

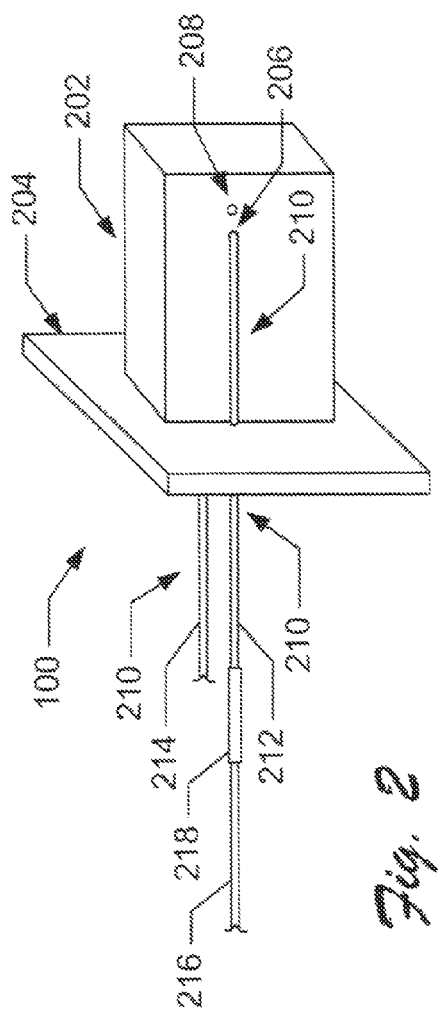
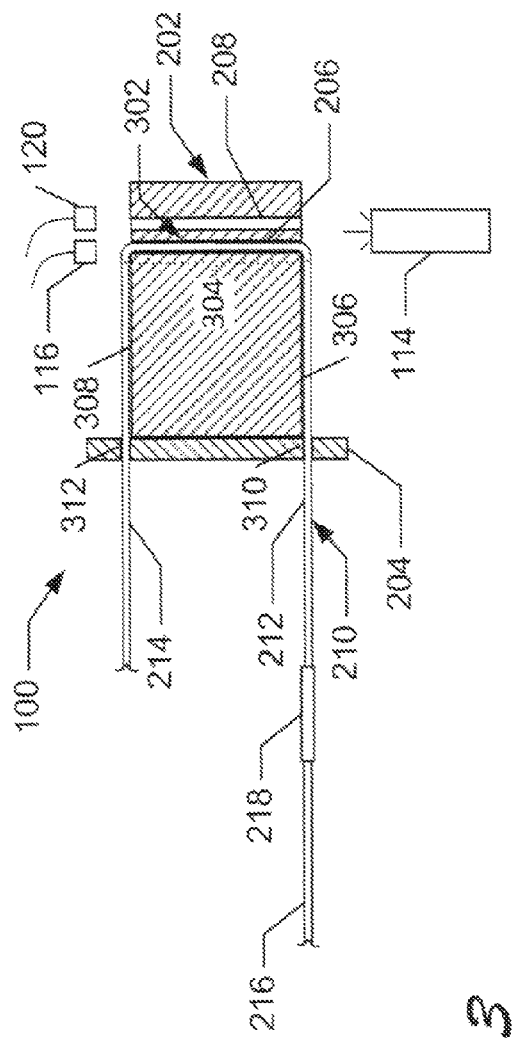

000# NANOFLOW DETECTOR CELL

BACKGROUND

Nano-liquid chromatography (nano-LC), or nanochromatography, is a miniaturized High Performance Liquid Chromatography (HPLC) technique carried out using a capillary column having an internal diameter between 10 and 350 nanometers. Using smaller internal diameter columns in HPLC enables increased detection sensitivity, reduced sample dilution and reduction of mobile phase flow-rates and consumption.

SUMMARY

The described nanoflow detection cell comprises a nanoflow detection cell template defining a sample channel transverse the template and a reference channel transverse the template. The reference channel is also generally parallel to the sample channel and spaced apart from the sample channel. Clear capillary tubing extends through the sample channel, defining a sample chamber. A portion of the capillary tubing extends out of each end of the sample channel and is shaped to the template.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is set forth with reference to the accompanying figures, in which the left-most digit of a reference number identifies the figure in which the reference number first appears. The use of the same reference numbers in different figures indicates similar or identical items or features.

FIG. 1 diagrammatically illustrates an example liquid chromatograph capable of employing an embodiment of the nanoflow detector cell described herein.

FIG. 2 is a partially fragmented diagrammatic perspective side view of an example nanoflow detector cell, according to one embodiment.

FIG. 3 is a fragmented, generally cross-sectional, diagrammatic top view of the example nanoflow detector cell of FIG. 1, shown in conjunction with a detector light source and photo-detectors.

DETAILED DESCRIPTION

Overview

Figure 4:
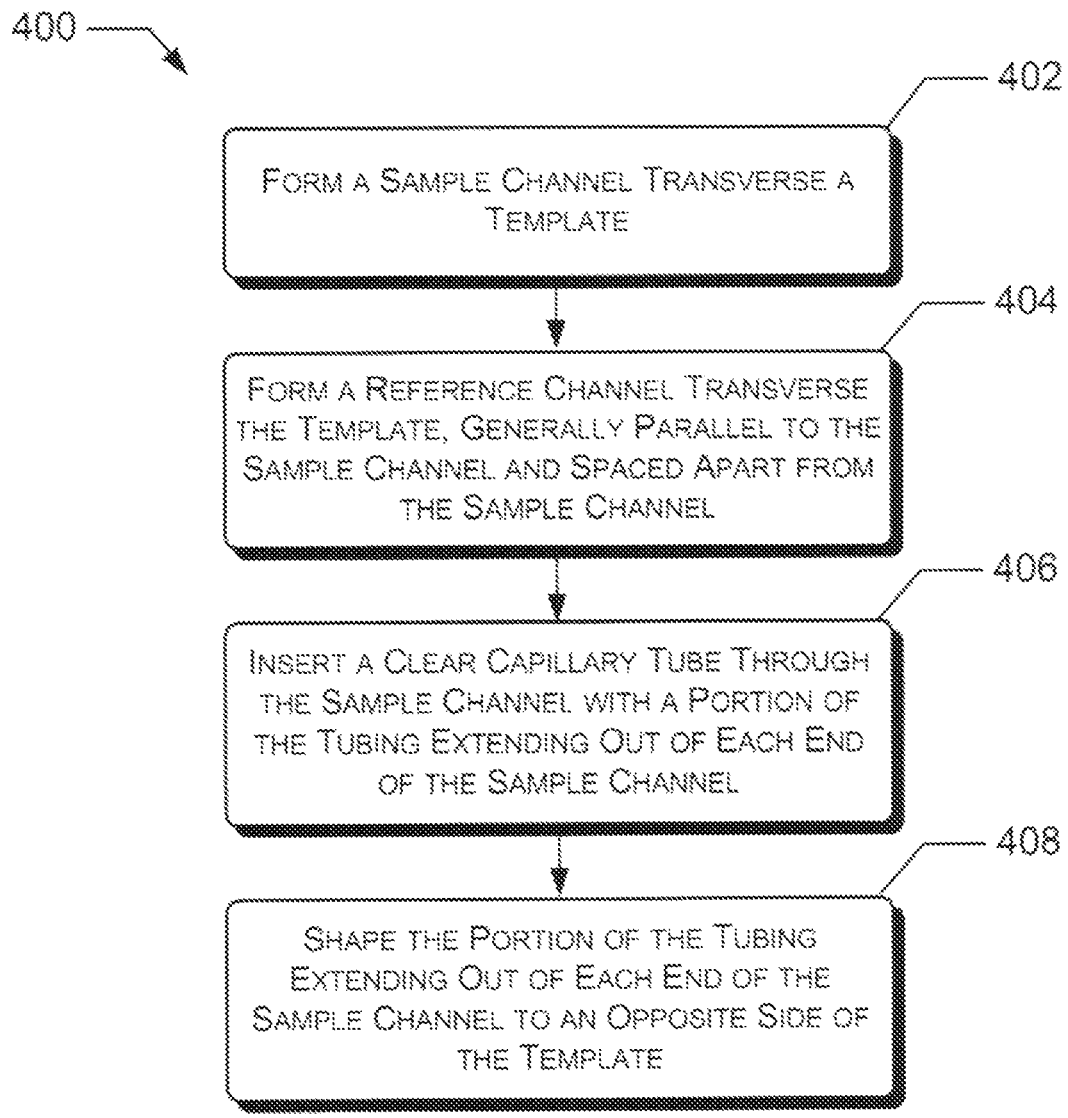
FIG. 4 shows an example procedure for fabricating a nanoflow detection cell, according to one embodiment.

The systems and methods described herein relate to a nanoflow detector cell, which may be used for nanochromatography. In certain implementations, the nanoflow detector cell is a nano-scale chromatography detector cell intended for use in (Ultraviolet) UV-visible detection in nanochromatography. In accordance with various implementations, the nanoflow detector cell includes a template, which may be sized for use in a HPLC UV-visible detector.

In one implementation, and to manufacture the present nanoflow detector cell, two one-millimeter diameter channels may be drilled (or otherwise formed) in this template to provide a reference chamber and a sample chamber. The length of the sample chamber of the nanoflow detector cell corresponds to the distance between the light source and the photo-detector of the detection instrument in which the cell can be used. The manufacturing procedure inserts fused silica capillary tubing, with an internal diameter in the 25-500 micrometers range, into the sample channel. Its shape is then adapted to the template shape to obtain a compact cell. This resulting nanoflow detector cell is easily deployable in a HPLC UV-visible detector in a manner similar to which a conventional detection cell is deployed.

The volume of the present nanoflow detector cell is substantially lower than volume of standard detection cells, depending on the inside diameter of the fused silica capillary tubing. For example, a nanoflow detector cell formed using 25 micrometers inside diameter tubing of 5 millimeter in length in accordance with various embodiments has a corresponding cell volume of less than 3 nanoliters. Also, in various implementations, the cell volume can be changed by using a fused silica capillary having a different inside diameter. Despite the very low volume of the present nanoflow detector cell, the longitudinal configuration of the sample chamber, with respect to the detector light beam, facilitates higher sensitivity than conventional perpendicular configured detection cells. The capillary tubing made of fused silica used in various implementations of the present nanoflow detector cell has excellent mechanical resistance, good chemical inertness and a very low internal diameter. Further, despite the very low volume, the present nanoflow detector cell has an excellent resistance to the high pressures usually encountered in HPLC and related techniques. Since the inlet and outlet of the present nanoflow detector cell are made using the same length of capillary tubing used to make as the cell itself, the cell's dead volume is drastically reduced. Also, since the inlet of the nanoflow detector cell and corresponding outlet of a capillary LC column or capillary electrophoresis device are made of similar capillary tubing, connections to the present nanoflow cell may be easily made using Teflon tubing, or the like.

Particular examples discussed herein are adapted for use in nanochromatography using UV-visible detection. However, the present nanoflow detector cell is well adapted for use in other types of nanochromatography detectors and/or any number of analytical instruments that may employ nano-flow rates, including but not limited to capillary electrophoresis devices, or the like.

An Exemplary Use of a Nanoflow Detector Cell for Nanochromatography

FIG. 1 diagrammatically illustrates an example liquid chromatograph capable of employing nanoflow detector cell 100 described herein, according to one embodiment. Chromatograph 102 comprises solvent reservoir 104 holding a non-polar solvent such as hexane or a polar solvent such as a mixture of water and an alcohol. Pump 106 is used to pressurize the solvent to a high pressure (e.g., up to four-hundred atmospheres) to force the solvent through HPLC column 108. The sample to be analyzed is injected into the solvent stream, by sample injector 110 above HPLC column 108. Column 108 is typically filled with tiny silica particles. The time for a sample to travel through column 108 to detector 112 is measured from the time at which the sample is injected to the point at which it is detected by detector 112. Different compounds have different retention times. For a particular compound, the retention time will vary depending on the pressure used (i.e. the flow rate of the solvent), the nature of the stationary phase of the compound, the composition of the solvent, and the temperature of the column. In accordance with the present implementations, detector 112 makes use of an embodiment of present nanoflow detector cell, such as example nanoflow detector cell 100. Here, output of the column 108 is coupled to an inlet of the detector cell 100. Detector 112 detects (e.g., via use of ultra-violet and/or visible light absorption) when a substance has passed through column 108. Compounds absorb light of various wavelengths. Thus, a beam of light emitted by light source 114 shining through the sample window of detection cell 100 may be picked-up by sample detector photocell 116 to provide a reading of how much of the light is absorbed, and at what wavelengths. The amount of light absorbed by the sample is dependent upon the amount of a particular compound that is passing through the beam at the time and the wavelength is dependent up on the composition. A reference beam of light emitted by light source 114 shining through a reference chamber of detection cell 100 may be picked-up by reference detector photocell 120 to provide a reference.

Signal output 122 from detector 112 is provided to processing unit 124 and may be presented as a series of "peaks" displayed on display 126. Each peak may represent a compound in the mixture passing through the detector and absorbing light. Thus, not only can column retention times be used to help identify the compounds present in a sample, the peaks may be used as a way to measure the quantities of the compounds present. For example, the area under a peak is proportional to the amount of a compound absorbing at the peak's wavelength that has passed through a detection chamber of cell 100. Due to the relatively small volume of the present sample chamber, a detector employing the present nanoflow chromatography cell 100 has greater relative sensitivity.

An Exemplary Nanoflow Detector Cell for Nanochromatography

FIG. 2 is a partially fragmented diagrammatic perspective view an example nanoflow detector cell 100 for nanochromatography, according to one embodiment. Nanoflow detection cell 100 is generally intended for use in a liquid chromatography detector to provide nano-liquid chromatography, such as described above. However, other uses may be considered. Nanoflow detection cell 100 may be an Ultraviolet, visible light, Ultraviolet-visible light, or similar detection cell; that is, a cell intended for use in an Ultraviolet, visible light, Ultraviolet-visible light, or similar, liquid chromatography detector.

Nanoflow detection cell 100 comprises template 202, which, in accordance with various implementations, is generally parallelepiped in shape, and/or otherwise shaped, and sized for use in the detection cell chamber of a selected liquid chromatograph detector. Template 202 may be made of aluminum, stainless steel, a polymer material, or the like, as appropriate for application in the selected liquid chromatography detector. Template 202 may comprise a flange portion and/or separate flange (204) may be secured to template 202.

Template 202 defines sample channel 206 transverse the template. Reference channel 208 is also defined transverse the template, generally parallel to sample channel 206, spaced apart from sample channel 206. To facilitate use in a selected liquid chromatography detector, sample channel 206 corresponds, i.e. is positioned in template 202 to correspond, to a light source of the detector at one end and a sample photo-detector at the other end. Likewise, reference channel 208, open at each end, corresponds to the same light source of the detector at one end and a reference photo-detector at the other end.

Clear capillary sample tubing 210, extends through sample channel 206 defining a nano-liquid chromatography sample chamber in sample channel 206, and given the corresponding location with respect to the light source of the selected detector, provides a nano-liquid chromatography sample window. Tubing 210 may be made of fused silica and generally cylindrical, and thus sample channel 206 and reference channel 208 may be generally cylindrical in cross-section for sample channel 206 to receive tubing 210. Alternatively, sample channel 206 and reference channel 208 may have another cross-sectional shape, such that sample channel 206 may accommodate tubing having a corresponding cross-section. In accordance with various implementations, the capillary sample tubing has an outside diameter of one millimeter or less, and an internal diameter in a range of twenty-five to five hundred micrometers. Thus, if the capillary sample tubing has a length of between five and twenty millimeters, the present nanoflow detection cell has a volume in the range between three nanoliters and four microliters. Such a nanoflow detector cell is robust and gives good results with a wide flowrate range. A portion of capillary sample tubing 210 extends out of each end of sample channel 206 and is shaped to template 202 to provide inlet tube 212 and outlet tube 214. For example, the portion of the capillary sample tubing extending out of each end of sample channel 206 may be shaped along a side of template 202.

Thus, the same capillary tubing makes up the inlet for connection between a capillary chromatographic column and the nanoflow detector cell, the longitudinal transparent sample window of the nanoflow detector cell, and the outlet of the nanoflow detector cell. The present nanoflow detector cell provides a longitudinal configuration for the sample window with a relatively long path for the light beam, allowing an optimal absorption by the sample, while still having a total cell volume that does not exceed a few nanoliters, depending on the fused silica capillary inside diameter. The present nanoflow detector cell is well adapted for use with capillary monolithic columns, which are made of fused silica tubing packed with a suitable polymeric material.

If a flange (204) is disposed across an end of template 202, or template 202 includes an integrated flange portion (204), the portion of the capillary sample tubing extending out of each end of the sample channel may be shaped to extend along the sides of template 202 and to extend through orifices in flange 204 to provide inlet tube 212 and outlet tube 214.

To connect nanoflow cell 100 to chromatograph column 108 (FIG. 1), connection between the column output 216 and cell input tube 212 may be made using a short length of polytetrafluoroethylene (PTFE) tubing (218) with an inside diameter slightly less than the outer diameter of fused silica capillary tubing 210. This enables easy and rapid fitting of a column capillary with the inlet capillary of the nanoflow cell with a very low dead volume and avoids the need for any metallic coupling components. Such PTFE tubing is known to be resistant and chemically inert to most solvents and mobile phases. If properly correlating diameter PTFE tubing is used, no leaks at the connection between the capillary column and the nanoflow detector cell inlet should arise, despite the high pressures used in nano-CL. Other flexible polymeric tubing such as ethylene-tetrafluoroethylene fluoropolymer (ETFE) tubing can be used. Another option for connecting column outlet 216 to the present nanoflow cell in certain implementations is the use of commercially available high pressure coupling kits, or the like, such as those made of polyether ether ketone (PEEK), that employ finger-tight fittings which can withstand pressures of up to two hundred bars.

FIG. 3 is a fragmented, generally cross-sectional, diagrammatic top view of example nanoflow detector cell 100 of FIG.

2. The portion of tubing 210 extending through sample channel 206 defines a nano-liquid chromatography sample chamber 302, which in turn provides nano-liquid chromatography sample window 304 of length generally corresponding to the distance between detector light source 114 and sample photo-detector 116. Similarly, reference channel 208 generally corresponds to detector light source 114 and reference photo-detector 120.

As noted above, if a flange (204) is disposed across an end of template 202, the portion of capillary sample tubing 210 extending out of each end of sample channel 206 may be shaped to extend along sides 306 and 308 of template 202 and to extend through orifices 310 and 312 in flange 204 to provide inlet tube 212 and outlet tube 214.

An Exemplary Procedure to Fabricate a Nanoflow Detector Cell

FIG. 4 shows example procedure 400 for fabricating a nanoflow detection cell 100 for use in a liquid chromatography detector to provide nano-liquid chromatography, according to one embodiment. Therein, procedure 400 comprises forming a sample channel transverse a template at 402. In accordance with various implementations, the sample channel is formed to correspond to a light source of the detector at one end and a sample photo-detector of the detector at the other end. At 404 a reference channel may be formed, transverse the template. This reference channel may be generally parallel to and spaced apart from the sample channel. In various implementations, the reference channel is formed, open at each end, to correspond to the light source at one end and a reference photo-detector at the other end. As noted, the sample and reference channels may be generally cylindrical, and hence may be formed by drilling the template. In accordance with various implementations, the channels may be formed in other manners, such as during a casting or forging of the template, by boring, or in other appropriate manners, particularly where non-circular cross-sectional shapes are desired.

At 406, a clear capillary tube is inserted through the sample channel to define a nano-liquid chromatography sample chamber in the sample channel. As a result, the capillary sample tubing defining a nano-liquid chromatography sample chamber provides a nano-liquid chromatography sample window. Any polymer coating, or the like, on the tubing may need to be stripped or otherwise removed from the capillary sample tubing, such as through heating the coated tubing, prior to inserting the tubing in the template at 406. A portion of the capillary sample tubing extends out of each end of the sample channel following insertion of the tubing into the sample channel at 406.

The portion of the capillary sample tubing extending out of each end of the sample channel is shaped by heating using a microburner to the corresponding sides of the template at 408 to provide an inlet tube and an outlet tube for the cell. If the template includes a flange portion, or a flange is disposed on an end of the template, such that the flange extends across an end of the template, the inlet tube and the outlet tube may be passed through orifices in the flange as a part of the shaping at 408, or as a part of installation of the flange. Disposition of the tubing through flange orifices may assist in retaining the formed shape of the tube along the sides of the template.

CONCLUSION

Although a nanoflow detector cell has been described in language specific to structural features and/or methodological operations or actions, it is understood that the implementations defined in the appended claims are not necessarily limited to the specific features or actions described. Rather, the specific features and operations of a nanoflow detector cell for use in nanochromatography are disclosed as exemplary forms of implementing the claimed subject matter.

The invention claimed is:

1. A nanoflow detection cell comprising:
a nanoflow detection cell template having a pair of transversely opposed sides, a sample channel being formed through the nanoflow detection cell template and extending transversely therethrough, extending between the pair of transversely opposed sides, a reference channel also being formed through the nanoflow detection cell template and extending transversely therethrough, extending between the pair of transversely opposed sides, the reference channel and the sample channel being positioned adjacent and parallel with respect to one another; and
clear capillary sample tubing having a central portion and a pair of opposed end portions, the central portion extending through the sample channel and defining a sample chamber, wherein each of the end portions of the clear capillary sample tubing extends from a respective open end of the sample channel and is held against, and extends along, a respective one of the transversely opposed sides of the nanoflow detection cell template external to the nanoflow detection cell template.

2. The nanoflow detection cell of claim 1 wherein the capillary sample tubing has an outside diameter of one millimeter or less, and an internal diameter in a range of 25 to 500 micrometers.

3. The nanoflow detection cell of claim 1 wherein the capillary sample tubing has a volume in the range between three nanoliters and four microliters.

4. The nanoflow detection cell of claim 1 wherein the template is generally parallelepiped and the portion of the capillary sample tubing extending out of each end of the sample channel is shaped along a side of the template.

5. The nanoflow detection cell of claim 1 wherein the template further comprises a flange portion and the portion of the capillary sample tubing extending out of each end of the sample channel and shaped to the template extends through orifices in the flange to provide an inlet and an outlet for the nanoflow detection cell.

6. The nanoflow detection cell of claim 1 wherein the sample channel corresponds to a light source of the detector at one end and a sample photo-detector of the detector at the other end, whereby, the capillary sample tubing defining a nano-liquid chromatography sample chamber provides a nano-liquid chromatography sample window.

7. The nanoflow detection cell of claim 1 wherein the reference channel is open at each end to correspond to a light source at one end and a reference photo-detector at the other end.

8. The nanoflow detection cell of claim 1 wherein the nanoflow detection cell is a nano-liquid chromatography ultraviolet nanoflow detection cell, a nano-liquid chromatography visible light nanoflow detection cell or a nano-liquid chromatography ultraviolet-visible light nanoflow detection cell.

9. The nanoflow detection cell of claim 1 wherein the sample channel and the reference channel are each generally cylindrical.

10. A method for fabricating a nanoflow detection cell, the method comprising:
forming a sample channel through a nanoflow detection cell template, the nanoflow detection cell template having a pair of transversely opposed sides, the sample channel extending transversely through the nanoflow detection cell template, extending between the pair of transversely opposed sides;

forming a reference channel through the nanoflow detection cell template, the reference channel extending transversely through the nanoflow detection cell template, extending between the pair of transversely opposed sides, the reference channel and the sample channel being positioned adjacent and parallel with respect to one another;

inserting a clear capillary tube through the sample channel, the clear capillary tube having a central portion and a pair of opposed end portions, the central portion defining a nano-liquid chromatography sample chamber in the sample channel, each said end portion of the capillary sample tubing extending out of a respective open end of the sample channel; and securing each of the end portions of the clear capillary tube to a respective one of the transversely opposed sides of the nanoflow detection cell template, such that each of the end portions extends therealong external to the nanoflow detection cell template, the end portions of the clear capillary tube respectively defining an inlet tube and an outlet tube.

11. The method of claim 10 wherein said sample channel and said reference channel are each cylindrical and each forming comprises drilling.

12. The method of claim 10 wherein the capillary sample tubing has an outside diameter of one millimeter or less and an internal diameter in a range of 25 micrometers to 500 micrometers.

13. The method of claim 10 wherein the capillary sample chamber has a volume in the range between three nanoliters and four microliters.

14. The method of claim 10 wherein the template is generally parallelepiped.

15. The method of claim 10 wherein the template further comprises a flange portion extending across an end of the template and the shaping further comprises passing the inlet tube and the outlet tube through a flange.

16. The method of claim 10 wherein:
the sample channel is formed to correspond to a light source of a detector receiving the nanoflow detection cell at one end and a sample photo-detector of the detector at the other end, whereby the capillary sample tubing defines a nano-liquid chromatography sample chamber providing a nano-liquid chromatography sample window; and
the reference channel is formed, open at each end, to correspond to a light source of a detector receiving the nanoflow detection cell at one end and a reference photo-detector of the detector at the other end.

17. The method of claim 10 wherein the nanoflow detection cell is a nano-liquid chromatography ultraviolet nanoflow detection cell, a nano-liquid chromatography visible light nanoflow detection cell or a nano-liquid chromatography ultraviolet-visible light nanoflow detection cell.

18. The method of claim 10, further comprising stripping a polymer coating from the capillary sample tubing prior to the inserting.

* * * * *